US008875391B2

(12) United States Patent
Pianca et al.

(10) Patent No.: US 8,875,391 B2
(45) Date of Patent: Nov. 4, 2014

(54) METHODS FOR MAKING LEADS WITH RADIALLY-ALIGNED SEGMENTED ELECTRODES FOR ELECTRICAL STIMULATION SYSTEMS

(75) Inventors: Anne Margaret Pianca, Santa Monica, CA (US); William George Orinski, Reno, NV (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 996 days.

(21) Appl. No.: 12/966,740

(22) Filed: Dec. 13, 2010

(65) Prior Publication Data

US 2011/0078900 A1   Apr. 7, 2011

Related U.S. Application Data

(63) Continuation-in-part of application No. 12/498,650, filed on Jul. 7, 2009.

(51) Int. Cl.
*H01R 43/00* (2006.01)
*A61N 1/05* (2006.01)

(52) U.S. Cl.
CPC ............. *A61N 1/05* (2013.01); *A61N 1/0534* (2013.01)
USPC ............ 29/883; 29/843; 29/844; 29/860; 29/876; 607/116

(58) Field of Classification Search
USPC ........... 29/842–844, 846–848, 857, 858, 860, 29/861, 874, 876, 882–884; 600/373, 393, 600/395; 607/115, 11, 116, 118
See application file for complete search history.

(56) References Cited

U.S. PATENT DOCUMENTS

| | | | |
|---|---|---|---|
| 3,972,548 | A | 8/1976 | Roseen et al. |
| 4,602,624 | A | 7/1986 | Naples et al. |
| 4,630,611 | A | 12/1986 | King |
| 4,744,370 | A | 5/1988 | Harris |
| 4,762,135 | A | 8/1988 | van der Puije et al. |

(Continued)

FOREIGN PATENT DOCUMENTS

| | | |
|---|---|---|
| EP | 0580928 A1 | 2/1994 |
| EP | 0650694 B1 | 7/1998 |

(Continued)

OTHER PUBLICATIONS

Cameron, T, "Safety and Efficacy of Spinal Cord Stimulation for the Treatment of Chronic Pain: a 20-year Literature Review," Journal of Neurosurgery, vol. 100, 3rd Supplement: Spine, pp. 254-267, Mar. 2004.

(Continued)

*Primary Examiner* — Donghai D Nguyen
(74) *Attorney, Agent, or Firm* — Lowe Graham Jones PLLC; Bruce E. Black

(57) ABSTRACT

A method of making a stimulation lead includes attaching multiple segmented electrodes to a carrier. Each of the segmented electrodes has a curved form extending over an arc in the range of 10 to 345 degrees. The method further includes attaching conductors to the segmented electrodes; forming the carrier into a cylinder with segmented electrodes disposed within the cylinder; molding a lead body around the segmented electrodes disposed on the carrier; and removing at least a portion of the carrier to separate the segmented electrodes.

18 Claims, 9 Drawing Sheets

(56) References Cited

U.S. PATENT DOCUMENTS

| | | | |
|---|---|---|---|
| 5,000,194 A | 3/1991 | van den Honert et al. |
| 5,016,646 A | 5/1991 | Gotthardt et al. |
| 5,135,001 A | 8/1992 | Sinofsky et al. |
| 5,199,433 A | 4/1993 | Metzger et al. |
| 5,374,285 A | 12/1994 | Vaiani et al. |
| 5,458,629 A | 10/1995 | Baudino et al. |
| 5,522,874 A | 6/1996 | Gates |
| 5,711,316 A | 1/1998 | Elsberry et al. |
| 5,713,922 A | 2/1998 | King |
| 5,800,350 A | 9/1998 | Coppleson et al. |
| 5,843,148 A | 12/1998 | Gijsbers et al. |
| 5,938,688 A | 8/1999 | Schiff |
| 5,987,361 A | 11/1999 | Mortimer |
| 6,018,684 A | 1/2000 | Bartig et al. |
| 6,134,478 A | 10/2000 | Spehr |
| 6,161,047 A | 12/2000 | King et al. |
| 6,167,311 A | 12/2000 | Rezai |
| 6,181,969 B1 | 1/2001 | Gord |
| 6,322,559 B1 | 11/2001 | Daulton et al. |
| 6,510,347 B2 | 1/2003 | Borkan |
| 6,516,227 B1 | 2/2003 | Meadows et al. |
| 6,556,873 B1 | 4/2003 | Smits |
| 6,564,078 B1 | 5/2003 | Marino et al. |
| 6,609,029 B1 | 8/2003 | Mann et al. |
| 6,609,032 B1 | 8/2003 | Woods et al. |
| 6,678,564 B2 | 1/2004 | Ketterl et al. |
| 6,723,113 B1 | 4/2004 | Shkolnik |
| 6,741,892 B1 | 5/2004 | Meadows et al. |
| 6,757,970 B1 | 7/2004 | Kuzma et al. |
| 7,027,852 B2 | 4/2006 | Helland |
| 7,047,081 B2 * | 5/2006 | Kuzma ............... 607/115 |
| 7,047,082 B1 | 5/2006 | Schrom et al. |
| 7,047,084 B2 | 5/2006 | Erickson et al. |
| 7,051,419 B2 | 5/2006 | Schrom et al. |
| 7,212,867 B2 | 5/2007 | Van Venrooij et al. |
| 7,292,890 B2 | 11/2007 | Whitehurst et al. |
| 7,489,971 B1 | 2/2009 | Franz |
| 7,668,601 B2 | 2/2010 | Hegland et al. |
| 7,761,165 B1 | 7/2010 | He et al. |
| 7,761,985 B2 | 7/2010 | Hegland et al. |
| 7,809,446 B2 | 10/2010 | Meadows |
| 7,840,188 B2 | 11/2010 | Kurokawa |
| 7,848,802 B2 | 12/2010 | Goetz |
| 7,856,707 B2 | 12/2010 | Cole |
| 7,860,570 B2 | 12/2010 | Whitehurst et al. |
| 7,974,705 B2 | 7/2011 | Zdeblick et al. |
| 7,979,140 B2 | 7/2011 | Schulman |
| 8,000,808 B2 | 8/2011 | Hegland et al. |
| 8,019,440 B2 | 9/2011 | Kokones et al. |
| 8,036,755 B2 | 10/2011 | Franz |
| 8,041,309 B2 | 10/2011 | Kurokawa |
| 8,099,177 B2 | 1/2012 | Dahlberg |
| 8,225,504 B2 | 7/2012 | Dye et al. |
| 8,295,944 B2 | 10/2012 | Howard et al. |
| 8,321,025 B2 | 11/2012 | Bedenbaugh |
| 8,583,237 B2 | 11/2013 | Bedenbaugh |
| 2002/0156513 A1 | 10/2002 | Borkan |
| 2002/0183817 A1 | 12/2002 | Van Venrooij et al. |
| 2004/0039434 A1 | 2/2004 | Schrom et al. |
| 2004/0059392 A1 | 3/2004 | Parramon et al. |
| 2005/0015130 A1 | 1/2005 | Gill |
| 2005/0038489 A1 | 2/2005 | Grill |
| 2005/0171587 A1 | 8/2005 | Daglow et al. |
| 2006/0025841 A1 | 2/2006 | McIntyre |
| 2006/0149335 A1 | 7/2006 | Meadows |
| 2006/0168805 A1 | 8/2006 | Hegland et al. |
| 2006/0173262 A1 | 8/2006 | Hegland et al. |
| 2006/0247697 A1 | 11/2006 | Sharma et al. |
| 2007/0150007 A1 | 6/2007 | Anderson et al. |
| 2007/0150036 A1 | 6/2007 | Anderson |
| 2007/0161294 A1 | 7/2007 | Brase et al. |
| 2007/0168008 A1 | 7/2007 | Olsen |
| 2007/0203537 A1 | 8/2007 | Goetz et al. |
| 2007/0203538 A1 | 8/2007 | Stone et al. |
| 2007/0203539 A1 | 8/2007 | Stone et al. |
| 2007/0203540 A1 | 8/2007 | Goetz et al. |
| 2007/0203541 A1 | 8/2007 | Goetz et al. |
| 2007/0203542 A1 | 8/2007 | Goetz et al. |
| 2007/0203543 A1 | 8/2007 | Stone et al. |
| 2007/0203544 A1 | 8/2007 | Goetz et al. |
| 2007/0203545 A1 | 8/2007 | Stone et al. |
| 2007/0203546 A1 | 8/2007 | Stone et al. |
| 2007/0219595 A1 | 9/2007 | He |
| 2007/0239243 A1 | 10/2007 | Moffitt et al. |
| 2007/0265664 A1 | 11/2007 | Gerber et al. |
| 2008/0071320 A1 | 3/2008 | Brase |
| 2008/0103574 A1 | 5/2008 | Gerber |
| 2008/0103580 A1 | 5/2008 | Gerber |
| 2008/0114230 A1 | 5/2008 | Addis |
| 2008/0140168 A1 | 6/2008 | Walter et al. |
| 2008/0215125 A1 | 9/2008 | Farah et al. |
| 2008/0269740 A1 | 10/2008 | Bonde et al. |
| 2008/0269854 A1 | 10/2008 | Hegland et al. |
| 2009/0012591 A1 | 1/2009 | Barker |
| 2009/0054936 A1 | 2/2009 | Eggen et al. |
| 2009/0054941 A1 | 2/2009 | Eggen et al. |
| 2009/0054946 A1 | 2/2009 | Sommer et al. |
| 2009/0054947 A1 | 2/2009 | Bourn et al. |
| 2009/0082640 A1 | 3/2009 | Kovach et al. |
| 2009/0082641 A1 | 3/2009 | Giftakis et al. |
| 2009/0082829 A1 | 3/2009 | Panken et al. |
| 2009/0083070 A1 | 3/2009 | Giftakis et al. |
| 2009/0105785 A1 | 4/2009 | Wei et al. |
| 2009/0112282 A1 | 4/2009 | Kast et al. |
| 2009/0187222 A1 | 7/2009 | Barker |
| 2009/0204192 A1 | 8/2009 | Carlton et al. |
| 2009/0204193 A1 | 8/2009 | Kokones et al. |
| 2009/0276021 A1 | 11/2009 | Meadows et al. |
| 2010/0036468 A1 | 2/2010 | Decre et al. |
| 2010/0076535 A1 | 3/2010 | Pianca et al. |
| 2010/0082076 A1 | 4/2010 | Lee et al. |
| 2010/0094387 A1 | 4/2010 | Pianca et al. |
| 2010/0268298 A1 | 10/2010 | Moffitt et al. |
| 2010/0269339 A1 | 10/2010 | Dye et al. |
| 2011/0005069 A1 | 1/2011 | Pianca |
| 2011/0047795 A1 | 3/2011 | Turner et al. |
| 2011/0056076 A1 | 3/2011 | Hegland et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0131808 A1 | 6/2011 | Gill |
| 2011/0238129 A1 | 9/2011 | Moffitt et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2013/0197424 A1 | 8/2013 | Bedenbaugh |
| 2013/0197602 A1 | 8/2013 | Pianca et al, |
| 2013/0261684 A1 | 10/2013 | Howard |
| 2013/0317587 A1 | 11/2013 | Barker |
| 2013/0325091 A1 | 12/2013 | Pianca et al. |

FOREIGN PATENT DOCUMENTS

| | | |
|---|---|---|
| EP | 0832667 B1 | 2/2004 |
| EP | 1181947 B1 | 1/2006 |
| EP | 2092952 A1 | 8/2009 |
| WO | 9732628 A1 | 9/1997 |
| WO | 9955411 A3 | 2/2000 |
| WO | 0038574 A1 | 7/2000 |
| WO | 02068042 A1 | 9/2002 |
| WO | 2004045707 A1 | 6/2004 |
| WO | 2008053789 A1 | 5/2008 |
| WO | 2009001327 A2 | 2/2009 |
| WO | 2009025816 A1 | 2/2009 |
| WO | 2009102536 A1 | 8/2009 |
| WO | 2010-055421 A1 | 5/2010 |

(56) References Cited

FOREIGN PATENT DOCUMENTS

OTHER PUBLICATIONS

Rosenow, J. M. et al., "Failure Modes of Spinal Cord Stimulation Hardware," Journal of Neurosurgery: Spine, vol. 5, No. 3, pp. 183-190, Sep. 2006.
U.S. Appl. No. 12/177,823, filed Jul. 22, 2008.
U.S. Appl. No. 61/170,037, filed Apr. 16, 2009.
U.S. Appl. No. 11/694,769, filed Mar. 30, 2007.
U.S. Appl. No. 11/855,033, filed Sep. 13, 2007.
U.S. Appl. No. 13/275,112, filed Oct. 17, 2011.
U.S. Appl. No. 13/363,059, filed Jan. 31, 2012.
U.S. Appl. No. 13/368,982, filed Feb. 8, 2012.
U.S. Appl. No. 13/369,013, filed Feb. 8, 2012.
U.S. Appl. No. 13/368,733, filed Feb. 8, 2012.
International Search Report and Written Opinion for International Patent Application No. PCT/US2011/058160 mailed Mar. 19, 2012.
U.S. Appl. No. 12/498,650 Official Communication mailed May 6, 2013.
U.S. Appl. No. 13/750,725, filed Jan. 25, 2013.
U.S. Appl. No. 13/787,171, filed Mar. 6, 2013.
U.S. Appl. No. 13/899,316, filed May 21, 2013.
U.S. Appl. No. 13/906,776, filed May 31, 2013.
International Search Report and Written Opinion for International Patent Application No. PCT/US2010/040995 mailed Jan. 18, 2011.
International Preliminary Report on Patentability for International Patent Application No. PCT/US2010/040995 mailed Jan. 19, 2012.
U.S. Appl. No. 13/951,057, filed Jul. 25, 2013.
U.S. Appl. No. 14/053,112, filed Oct. 14, 2013.
U.S. Appl. No. 12/498,650, Official Communication mailed Nov. 20, 2012.

* cited by examiner

METHODS FOR MAKING LEADS WITH RADIALLY-ALIGNED SEGMENTED ELECTRODES FOR ELECTRICAL STIMULATION SYSTEMS

CROSS REFERENCE TO RELATED APPLICATION

This application is a continuation-in-part of U.S. patent application Ser. No. 12/498,650, filed Jul. 7, 2009; the entire contents of which are incorporated herein by reference.

FIELD

The invention is directed to the area of electrical stimulation systems and methods of making and using the systems. The present invention is also directed to electrical stimulation leads with multiple sets of radially-aligned segmented electrodes, as well as methods of making and using the segmented electrodes, leads, and electrical stimulation systems.

BACKGROUND

Electrical stimulation can be useful for treating a variety of conditions. Deep brain stimulation can be useful for treating, for example, Parkinson's disease, dystonia, essential tremor, chronic pain, Huntington's Disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging ("MRI") or computerized tomography ("CT") scans can provide a starting point for determining where the stimulating electrode should be positioned to provide the desired stimulus to the target neurons.

After the lead is implanted into a patient's brain, electrical stimulus current can be delivered through selected electrodes on the lead to stimulate target neurons in the brain. Typically, the electrodes are formed into rings disposed on a distal portion of the lead. The stimulus current projects from the ring electrodes equally in every direction. Because of the ring shape of these electrodes, the stimulus current cannot be directed to one or more specific positions around the ring electrode (e.g., on one or more sides, or points, around the lead). Consequently, undirected stimulation may result in unwanted stimulation of neighboring neural tissue, potentially resulting in undesired side effects.

BRIEF SUMMARY

One embodiment is a method of making a stimulation lead that includes attaching multiple segmented electrodes to a carrier. Each of the segmented electrodes has a curved form extending over an arc in the range of 10 to 345 degrees. The method further includes attaching conductors to the segmented electrodes; forming the carrier into a cylinder with segmented electrodes disposed within the cylinder; molding a lead body around the segmented electrodes disposed on the carrier; and removing at least a portion of the carrier to separate the segmented electrodes.

Another embodiment is a method of making a stimulation lead that includes attaching multiple segmented electrodes to a carrier; attaching conductors to the segmented electrodes; forming the carrier into a cylinder with the segmented electrodes disposed within the cylinder; molding a lead body around the plurality of segmented electrodes disposed on the carrier; and grinding at least a portion of the carrier away to separate the segmented electrodes.

Yet another embodiment is a method of making a stimulation lead that includes attaching multiple segmented electrodes to a carrier. Each of the segmented electrodes comprises a corrugated interior surface. The method further includes attaching conductors to the segmented electrodes; forming the carrier into a cylinder with the segmented electrodes disposed within the cylinder; molding a lead body around the segmented electrodes disposed on the carrier; and removing at least a portion of the carrier to separate the segmented electrodes.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The invention is directed to the area of electrical stimulation systems and methods of making and using the systems. The present invention is also directed to forming electrical stimulation leads with multiple sets of radially-aligned segmented electrodes, as well as methods of making and using the segmented electrodes, leads, and electrical stimulation systems.

A lead for deep brain stimulation may include stimulation electrodes, recording electrodes, or a combination of both. A practitioner may determine the position of the target neurons using the recording electrode(s) and then position the stimulation electrode(s) accordingly without removal of a recording lead and insertion of a stimulation lead. In some embodiments, the same electrodes can be used for both recording and stimulation. In some embodiments, separate leads can be used; one with recording electrodes which identify target neurons, and a second lead with stimulation electrodes that replaces the first after target neuron identification. A lead may include recording electrodes spaced around the circumference of the lead to more precisely determine the position of the target neurons. In at least some embodiments, the lead is rotatable so that the stimulation electrodes can be aligned with the target neurons after the neurons have been located using the recording electrodes. For illustrative purposes, the leads are described herein relative to use for deep brain stimulation, but it will be understood that any of the leads can be used for applications other than deep brain stimulation.

Deep brain stimulation devices and leads are described in, for example, U.S. Patent Application Publication No. 2006/0149335 A1 ("Devices and Methods For Brain Stimulation"), U.S. patent application Ser. No. 12/237,888 ("Leads With Non-Circular-Shaped Distal Ends For Brain Stimulation Systems and Methods of Making and Using"), U.S. Patent Application Publication 2007/0150036 A1 ("Stimulator Leads and Methods For Lead Fabrication"), U.S. patent application Ser. No. 12/177,823 ("Lead With Transition and Methods of Manufacture and Use"), U.S. patent application Ser. No. 12/427,935 ("Electrodes For Stimulation Leads and Methods of Manufacture and Use"), U.S. patent application Ser. No. 61/170,037 ("Deep Brain Stimulation Current Steering with Split Electrodes"), U.S. patent application Ser. No. 61/022,953, U.S. patent application Ser. No. 61/316,759, and U.S. patent application Ser. No. 12/356,480. Each of these references is incorporated herein by reference.

Figure 1:
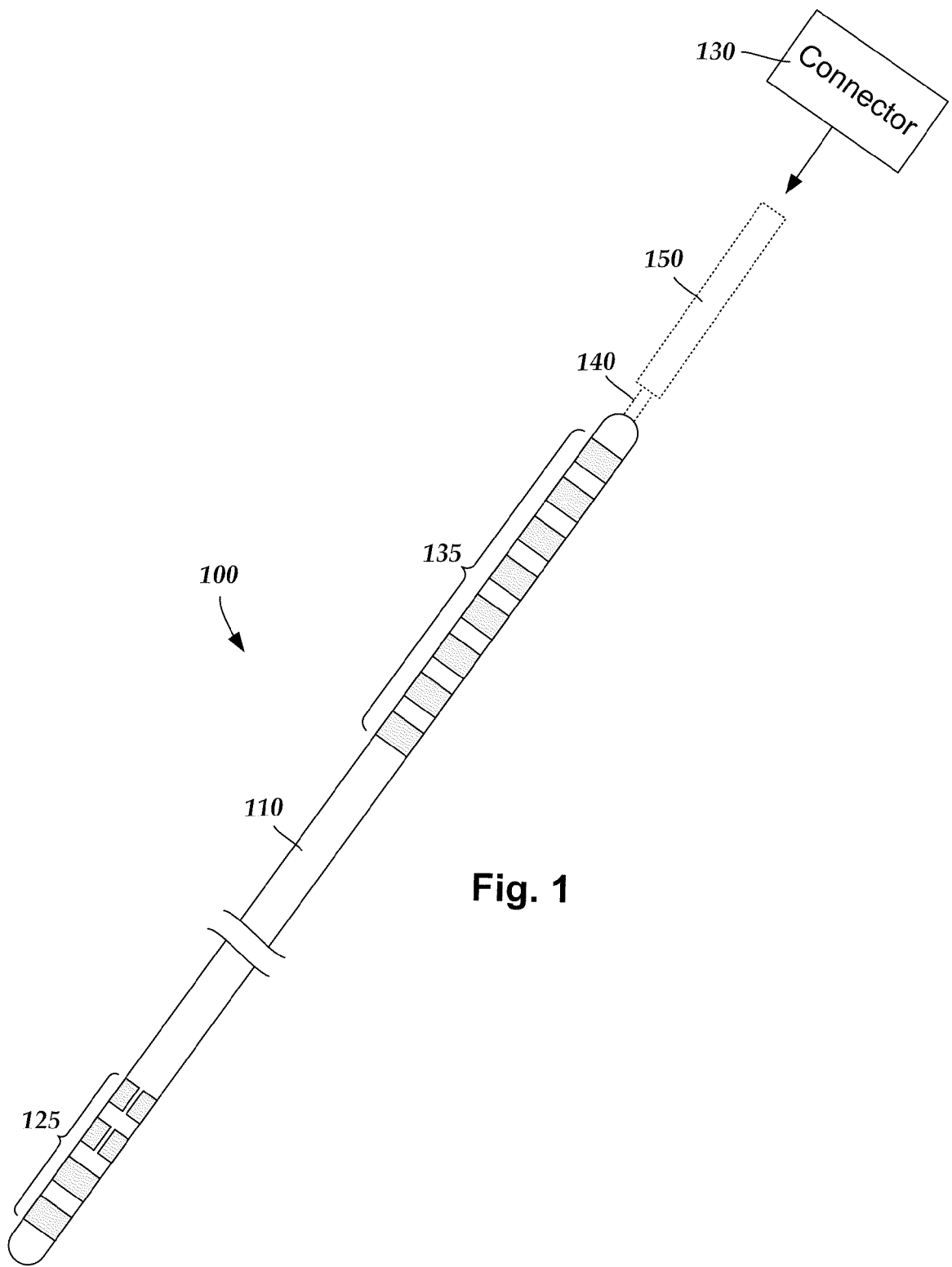
FIG. 1 is a schematic side view of one embodiment of a device for brain stimulation, according to the invention.

FIG. 1 illustrates one embodiment of a device 100 for brain stimulation. The device includes a lead 110, a plurality of electrodes 125 disposed at least partially about a circumference of the lead 110, a plurality of terminals 135, a connector 130 for connection of the electrodes to a control unit, and a stylet 140 for assisting in insertion and positioning of the lead in the patient's brain. The stylet 140 can be made of a rigid material. Examples of suitable materials for the stylet include, but are not limited to, tungsten, stainless steel, and rigid plastic. The stylet 140 may have a handle 150 to assist insertion into the lead 110, as well as rotation of the stylet 140 and lead 110. The connector 130 fits over a proximal end of the lead 110, preferably after removal of the stylet 140.

The control unit (not shown) is typically an implantable pulse generator that can be implanted into a patient's body, for example, below the patient's clavicle area. The pulse generator can have eight stimulation channels which may be independently programmable to control the magnitude of the current stimulus from each channel. In some cases the pulse generator may have more than eight stimulation channels (e.g., 16-, 32-, or more stimulation channels). The control unit may have one, two, three, four, or more connector ports, for receiving the plurality of terminals 135 at the proximal end of the lead 110.

In one example of operation, access to the desired position in the brain can be accomplished by drilling a hole in the patient's skull or cranium with a cranial drill (commonly referred to as a burr), and coagulating and incising the dura mater, or brain covering. The lead 110 can be inserted into the cranium and brain tissue with the assistance of the stylet 140. The lead 110 can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): insert the lead 110, retract the lead 110, or rotate the lead 110.

In some embodiments, measurement devices coupled to the muscles or other tissues stimulated by the target neurons, or a unit responsive to the patient or clinician, can be coupled to the control unit or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The lead 110 for deep brain stimulation can include stimulation electrodes, recording electrodes, or both. In at least some embodiments, the lead 110 is rotatable so that the stimulation electrodes can be aligned with the target neurons after the neurons have been located using the recording electrodes.

Stimulation electrodes may be disposed on the circumference of the lead 110 to stimulate the target neurons. Stimulation electrodes may be ring-shaped so that current projects from each electrode equally in every direction from the position of the electrode along a length of the lead 110. Ring electrodes, however, typically do not enable stimulus current to be directed to only one side of the lead. Segmented electrodes, however, can be used to direct stimulus current to one side, or even a portion of one side, of the lead. When segmented electrodes are used in conjunction with an implantable pulse generator that delivers constant current stimulus, current steering can be achieved to more precisely deliver the stimulus to a position around an axis of the lead (i.e., radial positioning around the axis of the lead).

To achieve current steering, segmented electrodes can be utilized in addition to, or as an alternative to, ring electrodes. Though the following description discusses stimulation electrodes, it will be understood that all configurations of the stimulation electrodes discussed may be utilized in arranging recording electrodes as well.

Figure 2:
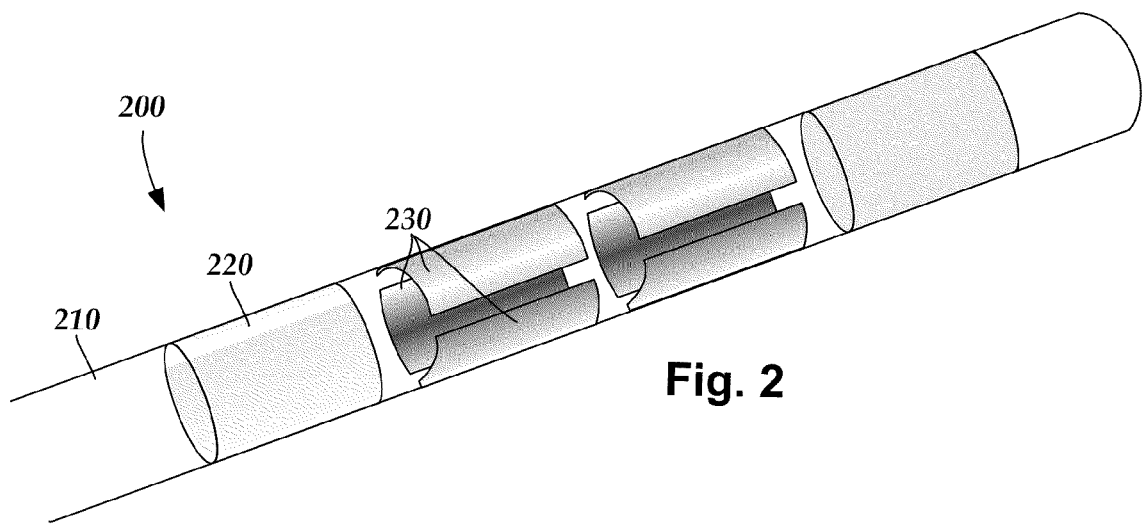
FIG. 2 is a schematic perspective view of one embodiment of a portion of a lead having a plurality of segmented electrodes, according to the invention.

FIG. 2 illustrates one embodiment of a distal portion of a lead 200 for brain stimulation. The lead 200 includes a lead body 210, one or more optional ring electrodes 220, and a plurality of sets of segmented electrodes 230. The lead body 210 can be formed of a biocompatible, non-conducting material such as, for example, a polymeric material. Suitable polymeric materials include, but are not limited to, silicone, polyurethane, polyurea, polyurethane-urea, polyethylene, or the like. Once implanted in the body, the lead 200 may be in contact with body tissue for extended periods of time. In at least some embodiments, the lead 200 has a cross-sectional diameter of no more than 1.5 mm and may be in the range of 1 to 1.5 mm. In at least some embodiments, the lead 200 has a length of at least 10 cm and the length of the lead 200 may be in the range of 25 to 70 cm.

The electrodes may be made using a metal, alloy, conductive oxide, or any other suitable conductive biocompatible material. Examples of suitable materials include, but are not limited to, platinum, platinum iridium alloy, iridium, titanium, tungsten, palladium, or the like. Preferably, the electrodes are made of a material that is biocompatible and does not substantially corrode under expected operating conditions in the operating environment for the expected duration of use.

Each of the electrodes can either be used or unused (OFF). When the electrode is used, the electrode can be used as an anode or cathode and carry anodic or cathodic current. In some instances, an electrode might be an anode for a period of time and a cathode for a period of time.

Stimulation electrodes in the form of ring electrodes 220 may be disposed on any part of the lead body 210, usually near a distal end of the lead 200. In FIG. 2, the lead 200 includes two ring electrodes 220. Any number of ring electrodes 220 may be disposed along the length of the lead body 210 including, for example, one, two three, four, five, six, seven, eight, nine, ten, eleven, twelve, thirteen, fourteen, fifteen, sixteen or more ring electrodes 220. It will be understood that any number of ring electrodes may be disposed along the length of the lead body 210. In some embodiments, the ring electrodes 220 are substantially cylindrical and wrap around the entire circumference of the lead body 210. In some embodiments, the outer diameters of the ring electrodes 220 are substantially equal to the outer diameter of the lead body 210. The length of the ring electrodes 220 may vary according to the desired treatment and the location of the target neurons. In some embodiments the length of the ring electrodes 220 are less than or equal to the diameters of the ring electrodes 220. In other embodiments, the lengths of the ring electrodes 220 are greater than the diameters of the ring electrodes 220.

Deep brain stimulation leads may include one or more sets of segmented electrodes. Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a radially segmented electrode array ("RSEA"), current steering can be performed not only along a length of the lead but also around a circumference of the lead. This provides precise three-dimensional targeting and delivery of the current stimulus to neural target tissue, while potentially avoiding stimulation of other tissue.

In FIG. 2, the lead 200 is shown having a plurality of segmented electrodes 230. Any number of segmented electrodes 230 may be disposed on the lead body 210 including, for example, one, two three, four, five, six, seven, eight, nine, ten, eleven, twelve, thirteen, fourteen, fifteen, sixteen or more segmented electrodes 230. It will be understood that any number of segmented electrodes 230 may be disposed along the length of the lead body 210.

The segmented electrodes 230 may be grouped into sets of segmented electrodes, where each set is disposed around a circumference of the lead 200 at a particular longitudinal portion of the lead 200. The lead 200 may have any number segmented electrodes 230 in a given set of segmented electrodes. The lead 200 may have one, two, three, four, five, six, seven, eight, or more segmented electrodes 230 in a given set. In at least some embodiments, each set of segmented electrodes 230 of the lead 200 contains the same number of segmented electrodes 230. The segmented electrodes 230 disposed on the lead 200 may include a different number of electrodes than at least one other set of segmented electrodes 230 disposed on the lead 200.

The segmented electrodes 230 may vary in size and shape. In some embodiments, the segmented electrodes 230 are all of the same size, shape, diameter, width or area or any combination thereof. In some embodiments, the segmented electrodes 230 of each circumferential set (or even all segmented electrodes disposed on the lead 200) may be identical in size and shape.

Each set of segmented electrodes 230 may be disposed around the circumference of the lead body 210 to form a substantially cylindrical shape around the lead body 210. The spacing between individual electrodes of a given set of the segmented electrodes may be the same, or different from, the spacing between individual electrodes of another set of segmented electrodes on the lead 200. In at least some embodiments, equal spaces, gaps or cutouts are disposed between each segmented electrode 230 around the circumference of the lead body 210. In other embodiments, the spaces, gaps or cutouts between the segmented electrodes 230 may differ in size or shape. In other embodiments, the spaces, gaps, or cutouts between segmented electrodes 230 may be uniform for a particular set of the segmented electrodes 230, or for all sets of the segmented electrodes 230. The sets of segmented electrodes 230 may be positioned in irregular or regular intervals along a length the lead body 210.

Conductors that attach to the ring electrodes 220 or segmented electrodes 230 extend along the lead body 210. These conductors may extend through the material of the lead 200 or along one or more lumens defined by the lead 200, or both. The conductors are presented at a connector (via terminals) for coupling of the electrodes 220, 230 to a control unit (not shown).

Figure 3A:
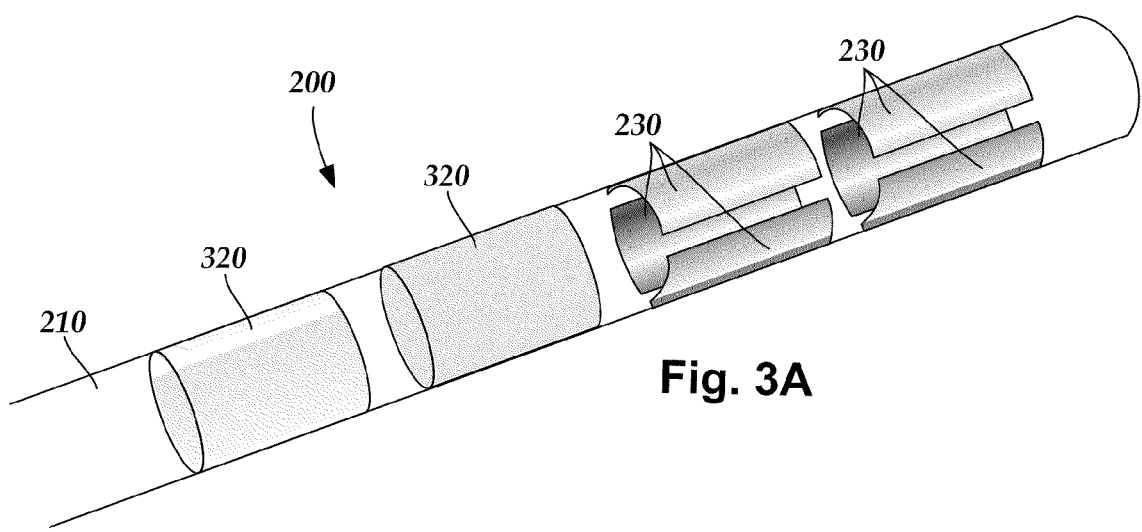
FIG. 3A is a perspective view of a third embodiment of a portion of a lead having a plurality of segmented electrodes, according to the invention.
Figure 3B:
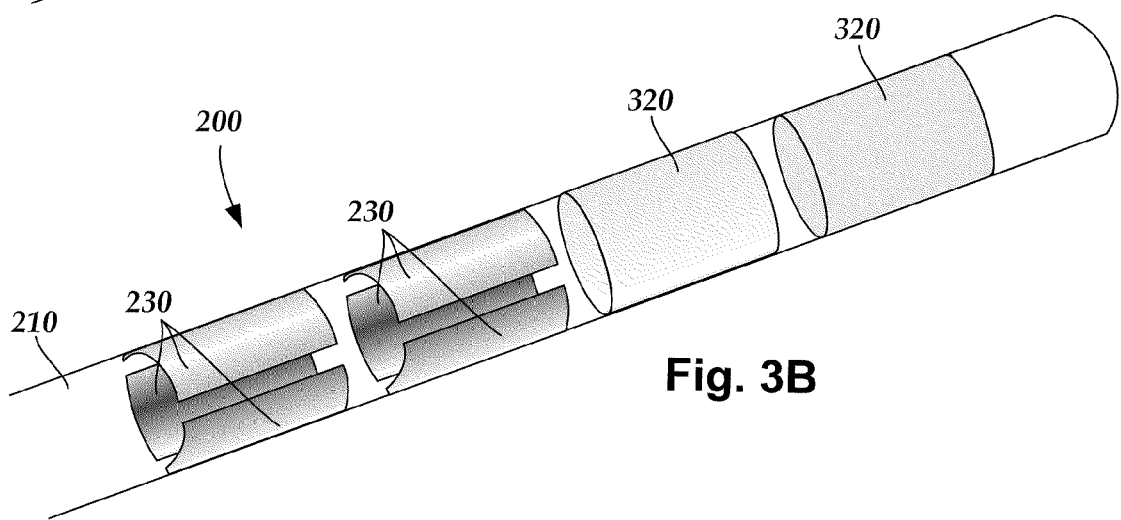
FIG. 3B is a perspective view of a fourth embodiment of a portion of a lead having a plurality of segmented electrodes, according to the invention.

When the lead 200 includes both ring electrodes 220 and segmented electrodes 230, the ring electrodes 220 and the segmented electrodes 230 may be arranged in any suitable configuration. For example, when the lead 200 includes two sets of ring electrodes 220 and two sets of segmented electrodes 230, the ring electrodes 220 can flank the two sets of segmented electrodes 230 (see e.g., FIG. 2). Alternately, the two sets of ring electrodes 220 can be disposed proximal to the two sets of segmented electrodes 230 (see e.g., FIG. 3A), or the two sets of ring electrodes 220 can be disposed distal to the two sets of segmented electrodes 230 (see e.g., FIG. 3B). It will be understood that other configurations are possible as well (e.g., alternating ring and segmented electrodes, or the like).

By varying the location of the segmented electrodes 230, different coverage of the target neurons may be selected. For example, the electrode arrangement of FIG. 3A may be useful if the physician anticipates that the neural target will be closer to a distal tip of the lead body 210, while the electrode arrangement of FIG. 3B may be useful if the physician anticipates that the neural target will be closer to a proximal end of the lead body 210.

Any combination of ring electrodes 220 and segmented electrodes 230 may be disposed on the lead 200. For example, the lead may include a first ring electrode, two sets of segmented electrodes, each set formed of three segmented electrodes 230, and a final ring electrode at the end of the lead. This configuration may simply be referred to as a 1-3-3-1 configuration. It may be useful to refer to the electrodes with this shorthand notation. Thus, the embodiment of FIG. 3A may be referred to as a 3-3-1-1 configuration, while the embodiment of FIG. 3B may be referred to as a 1-1-3-3 configuration. Other eight-electrode configurations include, for example, a 2-2-2-2 configuration, where four sets of segmented electrodes are disposed on the lead, and a 4-4 configuration, where two sets of segmented electrodes, each having four segmented electrodes 230 are disposed on the lead. In some embodiments, the lead includes 16 electrodes. Possible configurations for a 16-electrode lead include, but are not limited to 4-4-4-4; 8-8; 3-3-3-3-3-1 (and all rearrangements of this configuration); and 2-2-2-2-2-2-2-2.

Figure 4:
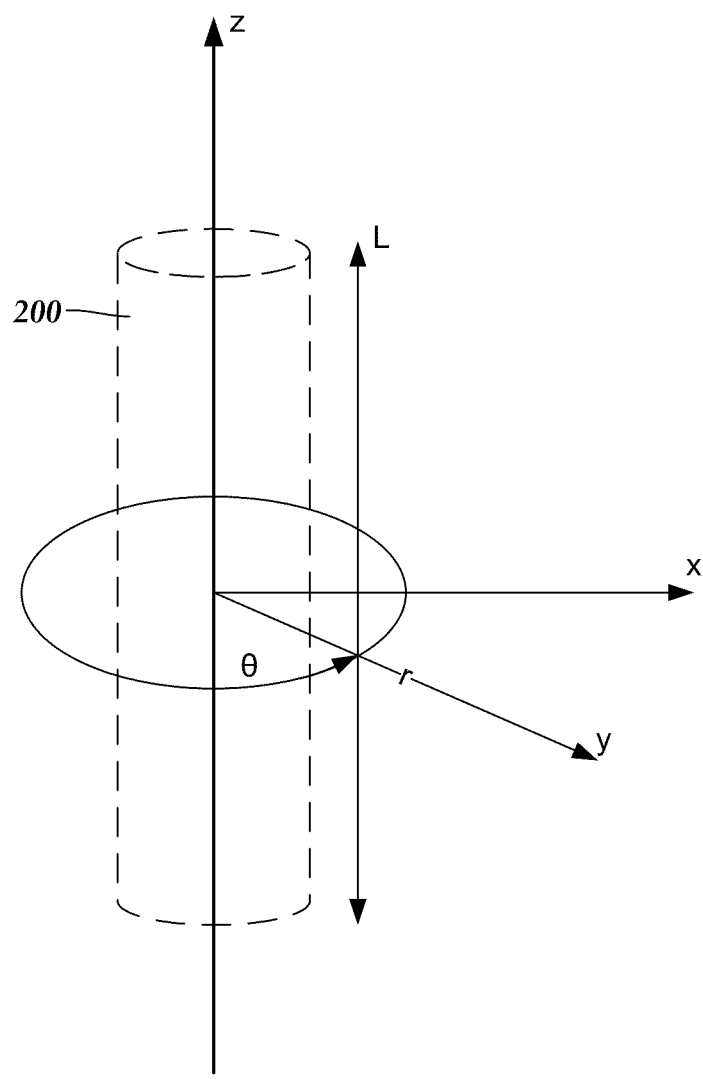
FIG. 4 is a schematic diagram of radial current steering along various electrode levels along the length of a lead, according to the invention.

FIG. 4 is a schematic diagram to illustrate radial current steering along various electrode levels along the length of the lead 200. While conventional lead configurations with ring electrodes are only able to steer current along the length of the lead (the z-axis), the segmented electrode configuration is capable of steering current in the x-axis, y-axis as well as the z-axis. Thus, the centroid of stimulation may be steered in any direction in the three-dimensional space surrounding the lead 200. In some embodiments, the radial distance, r, and the angle θ around the circumference of the lead 200 may be dictated by the percentage of anodic current (recognizing that stimulation predominantly occurs near the cathode, although strong anodes may cause stimulation as well) introduced to each electrode. In at least some embodiments, the configuration of anodes and cathodes along the segmented electrodes allows the centroid of stimulation to be shifted to a variety of different locations along the lead 200.

As can be appreciated from FIG. 4, the centroid of stimulation can be shifted at each level along the length of the lead 200. The use of multiple sets of segmented electrodes at different levels along the length of the lead allows for three-dimensional current steering. In some embodiments, the sets of segmented electrodes are shifted collectively (i.e., the centroid of simulation is similar at each level along the length of the lead). In at least some other embodiments, each set of segmented electrodes is controlled independently. Each set of segmented electrodes may contain two, three, four, five, six, seven, eight or more segmented electrodes. It will be understood that different stimulation profiles may be produced by varying the number of segmented electrodes at each level. For example, when each set of segmented electrodes includes only two segmented electrodes, uniformly distributed gaps (inability to stimulate selectively) may be formed in the stimulation profile. In some embodiments, at least three segmented electrodes 230 in a set are utilized to allow for true 360° selectivity.

As previously indicated, the foregoing configurations may also be used while utilizing recording electrodes. In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrodes to further identify the target neurons and facilitate positioning of the stimulation electrodes. For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The reliability and durability of the lead will depend heavily on the design and method of manufacture. Fabrication techniques discussed below provide methods that can produce manufacturable and reliable leads.

When the lead 200 includes a plurality of sets of segmented electrodes 230, it may be desirable to form the lead 200 such that corresponding electrodes of different sets of segmented electrodes 230 are radially aligned with one another along the length of the lead 200 (see e.g., the segmented electrodes 230 shown in FIG. 2). Radial alignment between corresponding electrodes of different sets of segmented electrodes 230 along the length of the lead 200 may reduce uncertainty as to the location or orientation between corresponding segmented electrodes of different sets of segmented electrodes. Accordingly, it may be beneficial to form electrode arrays such that corresponding electrodes of different sets of segmented electrodes along the length of the lead 200 are radially aligned with one another and do not radially shift in relation to one another during manufacturing of the lead 200.

Figure 5:
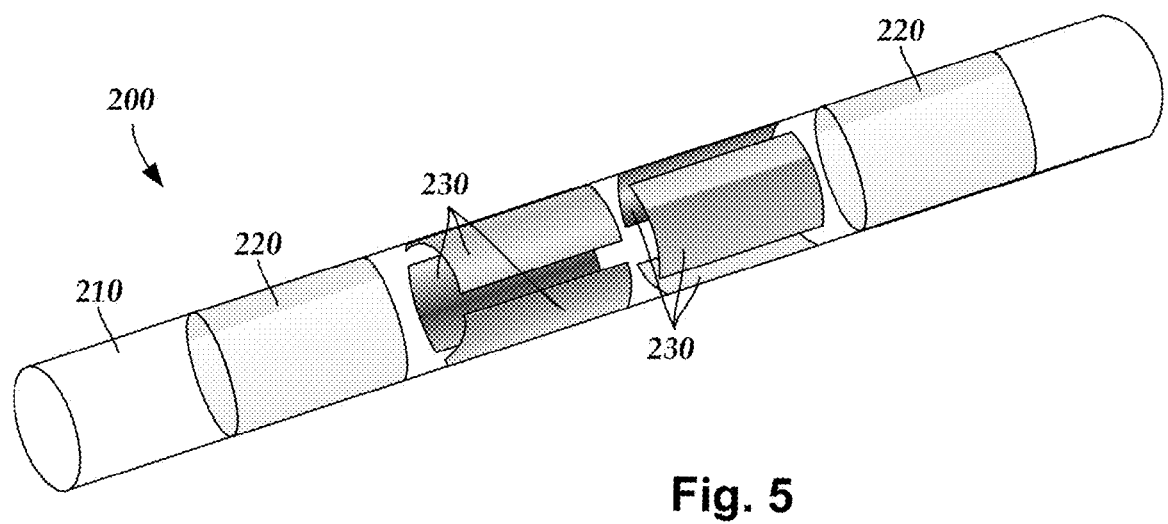
FIG. 5 is a perspective view of another embodiment of a portion of a lead having a plurality of segmented electrodes arranged in a staggered orientation, according to the invention.

FIG. 5 is a side view of another embodiment of the lead 200 having a plurality of sets of segmented electrodes. As shown in FIG. 5, individual electrodes in the two sets of segmented electrodes 230 are staggered relative to one another along the length of the lead body 210. In some cases, the staggered positioning of corresponding electrodes of different sets of segmented electrodes along the length of the lead 200 may be designed for a specific application.

Corresponding electrodes of at least two different sets of segmented electrodes can be radially aligned with one another along the length of the lead by disposing tabs on at least some of the electrodes and stringing an elongated member (e.g., one or more conductors, or the like) through one or more guides formed in one or more of the tabs disposed along different sets of the segmented electrodes. Corresponding electrodes of different sets of segmented electrodes can be radially aligned with one another along the length of the lead by disposing one or more electrode on membranes configured and arranged to couple to the lead. It will be understood that radially-aligning segmented electrodes along the length of the lead can be applied to either all, or only some, of the total number of segmented electrodes disposed on the lead.

Figure 6:
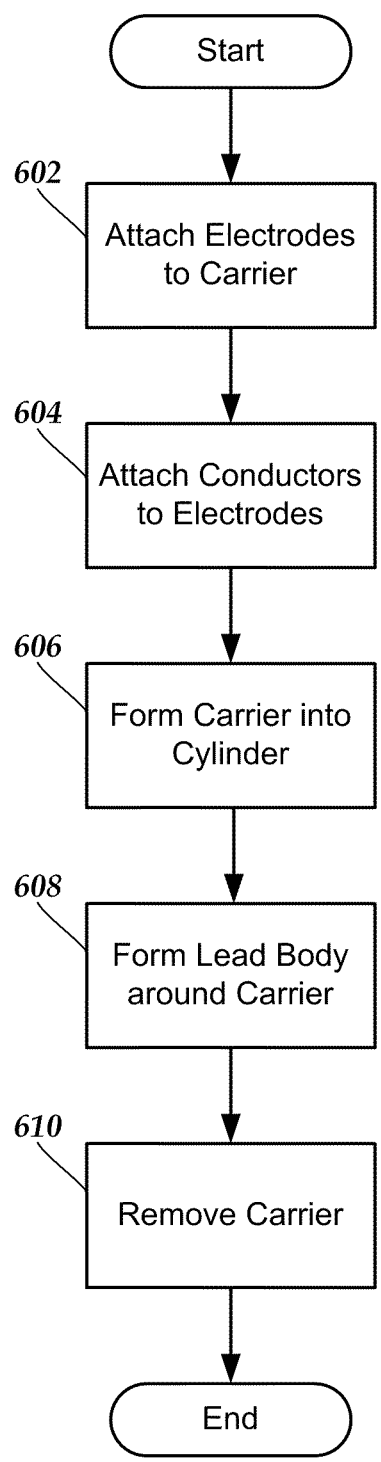
FIG. 6 is a flowchart of one embodiment of a method of making a lead, according to the invention.

A lead with segmented electrodes can be made in variety of different ways. FIG. 6 is a flowchart describing an embodiment of a method of making a lead with segmented electrodes. Beginning at step 602, multiple electrodes 702, 704 are attached to a carrier 706, as illustrated, for example, in FIG. 7A. In particular, multiple segmented electrodes 702 are attached to the carrier in an arrangement that, when the carrier is formed into a cylinder, result in the segmented electrodes being positioned in the desired arrangement (e.g., as one or more sets of segmented electrodes as illustrated, for example, in FIGS. 2, 3A, 3B, and 5) on the lead. The segmented electrodes 702 can be formed in any suitable shape or size and can be formed of the materials described above. In at least some embodiments, the segmented electrodes have a curved shape. The curved shape preferably corresponds to the curvature of the lead. For example, the curved shape of the segmented electrodes can have an arc of at least 10, 15, 20, 30, 40, 50, or 60 degrees. The arc of the segmented electrode may be no more than 345, 330, 320, 300, 270, 180, or 175 degrees. In some instance, the arc of the segmented electrodes is in the range of 10 to 345 degrees or in the range of 30 to 300 degrees or in the range of 50 to 180 degrees or in the range of 15 to 175 degrees.

Figure 8:
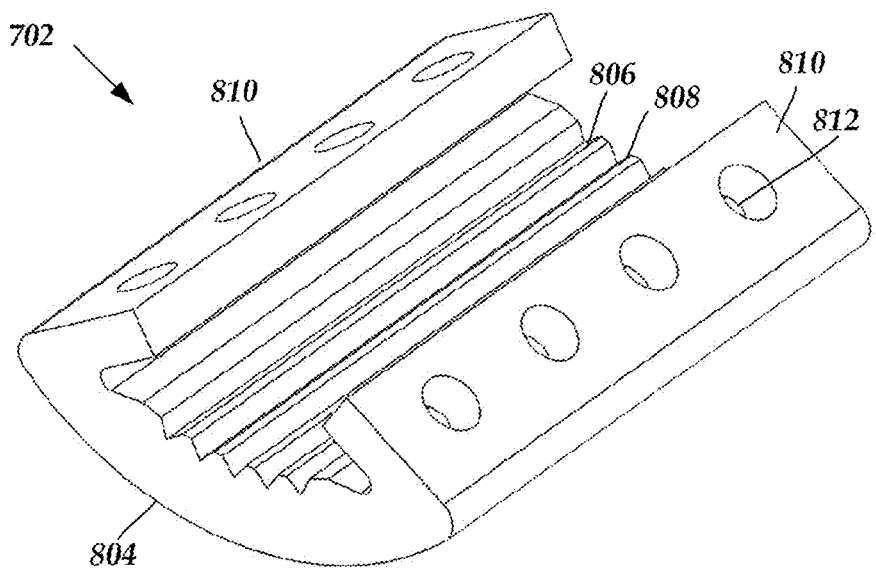
FIG. 8 is a schematic perspective view of a segmented electrode, according to the invention.

The segmented electrodes 702 optionally include one or more additional features to aid in holding the segmented electrode within the lead. One embodiment of a segmented electrode 702 displaying several optional features is provided in FIG. 8. The segmented electrode includes a stimulation surface 804 that, when the lead is formed and inserted into the patient, will be exposed to patient tissue. The segmented electrode also includes an interior surface 806 opposing the stimulation surface 804. The interior surface 806 will be in the interior the lead. One optional feature that aids in anchoring the segmented electrode 702 within the lead is a corrugated, or otherwise rough or non-uniform, texture 808 of the interior surface 806. The non-uniform texture 808 of the interior surface 806 increases the surface area that contacts the material of the lead body that is formed around the segmented electrode 702, as described below, and helps in retaining the segmented electrode within the lead. The corrugation of the texture 808 can have a triangular cross-section, as illustrated in FIG. 8, or any other suitable shape including, but not limited, a square, rectangular, trapezoidal, hemispherical, hexagonal, or any other regular or irregular cross-section. Other examples of suitable non-uniform textures include, but are not limited to, a checkerboard arrangement that is similar to corrugation but with intersecting grooves, an arrangement with multiple cleat-like projections or dimples extending from the surface 806, or a surface with a texture formed by knurling, grit blasting, or other methods of roughening of the surface, and the like.

Another optional feature of the segmented electrode 702 is one or more anchoring tabs 810. The anchoring tabs 810 are arranged so that they project into the interior of the lead and into the material of the lead body that is formed around the segmented electrode. The anchoring tabs can have any suitable size or shape and may optionally include one or more holes 812 in the tabs. In at least some embodiments, material from the lead body may flow into the holes 812 during the molding process to provide additional anchoring. When the segmented electrode 702 includes more than one anchoring tab 810, the anchoring tabs may be arranged around the segmented electrode in any suitable arrangement. For example, as illustrated in FIG. 8, two anchoring tabs 810 may extend from opposing sides towards each other. In other embodiments, the two anchoring tabs may extend from only a portion of a particular side of the segmented electrode 702. For example, two anchoring tabs may extend from the segmented electrode 702 with one tab extending near one end of a side of the electrode and the other tab extending near the other end of the opposing side of the electrode so that the two tabs are diagonally opposed. It will be understood that other arrangements can be used including, for example, arrangements in which tabs are directly opposed.

Figure 7A:
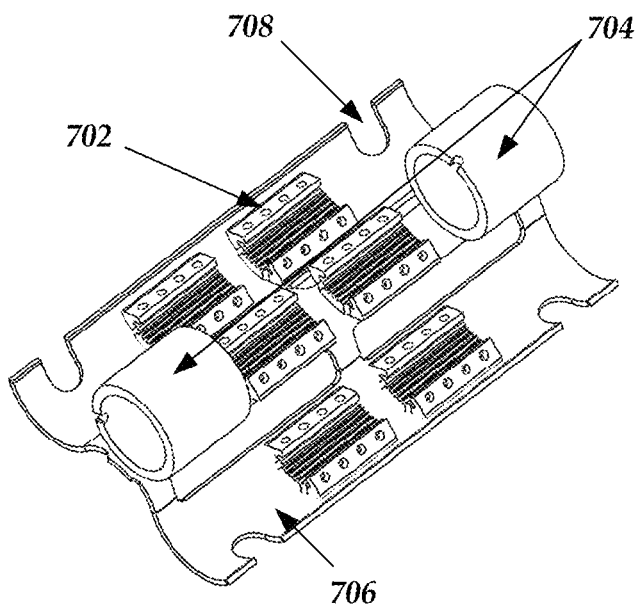
FIG. 7A is a schematic perspective view of one embodiment of electrodes disposed on a carrier, according to the invention.

Returning to FIG. 7A, optionally one or more ring electrodes 704 may be used. These ring electrodes can be positioned at the ends of the carrier, as illustrated in FIG. 7A, or between sets of segmented electrodes, or any combination thereof. It will be recognized that some embodiments may not include ring electrodes (including, for example, the embodiment of FIGS. 9A and 9B described further below.)

The carrier 706 is a temporary structure to which the electrodes 702, 704 are attached for manufacture of the lead. The carrier is typically relatively thin and can be made of any suitable material that is sufficiently flexible to be formed into a cylinder as described below. Such materials include, but are not limited to, metals (e.g., iron, aluminum, and the like), alloys (e.g., MP35N, steel, stainless steel, and the like), and plastics (e.g., plastic films such as those used for flexible circuits such as polyimide, polyetheretherketone (PEEK), polyetherimide, polyethylene naphthalate, polyethylene terephthalate, other polyesters, fluoropolymers, and the like). In at least some embodiments, the carrier may be flat (see, e.g., FIG. 9A) or the carrier may be formed into one or more curved sections (see, e.g., FIGS. 7A and 7B) in anticipation of forming a cylinder, as described below.

The electrodes 702, 704 can be attached to the carrier 706 by any suitable method including, but not limited to, welding, soldering, mounting using an adhesive (e.g., an epoxy), and the like. It will be understood that selection of a carrier material may limit the method of attachment of the electrodes to the carrier or selection of the method of attachment may limit the carrier material that can be used. Preferably, the carrier material (and any supplemental material, such as a solder or adhesive used to attach the electrodes to the carrier) is biocompatible as small amounts of such materials may remain on the finished lead.

The carrier 706 may include one or more features, such as slots 708 and tabs (see FIG. 9A for tabs 910), to facilitate formation of the carrier into a cylinder, as described below. Such features may act, for example, as tooling aids or registration aids or a combination thereof.

Figure 7B:
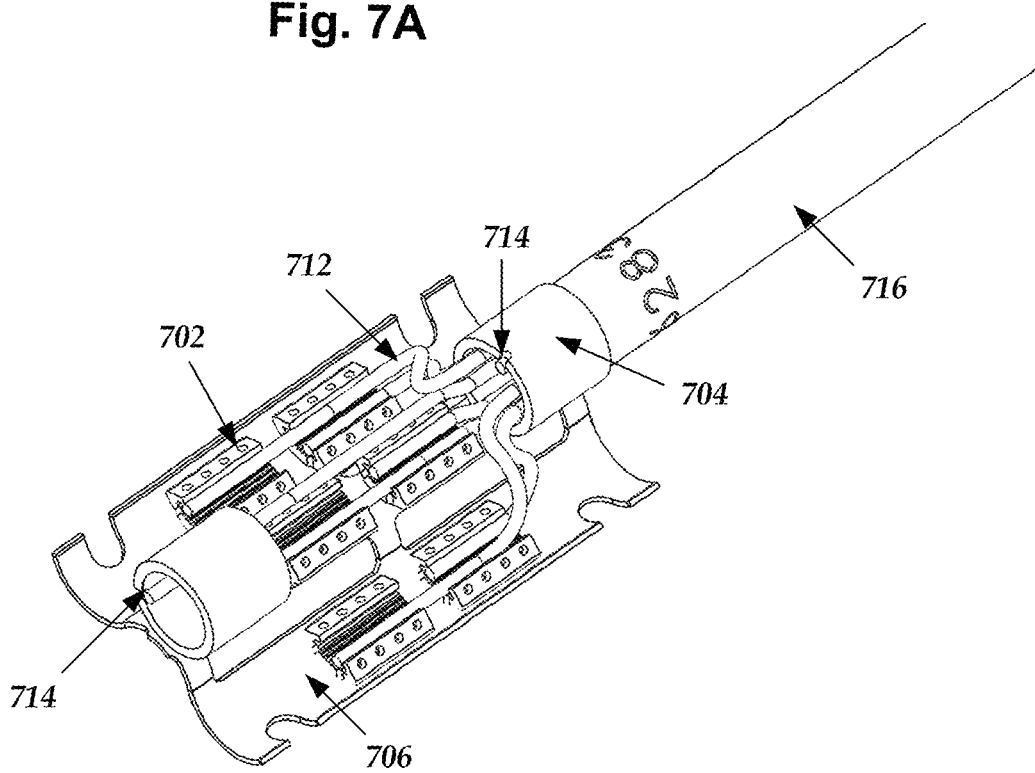
FIG. 7B is a schematic perspective view of conductors attached to the electrodes of FIG. 7A, according to the invention.

After attachment of the electrodes 702, 704 to the carrier 706, conductors 712 are attached to the electrodes 702, 704 (step 604 of FIG. 6) as illustrated, for example, in FIG. 7B. The conductors 712 can be, for example, insulated wires with a portion of the insulation removed to make contact with the electrodes 702, 704. A different conductor 712 can be attached to each electrode 702, 704, as illustrated in FIG. 7B. In other embodiments, the same conductor may be attached to two or more of the electrodes. The conductors 712 can be attached by any suitable method including, but not limited to, welding, soldering, crimping, using a conductive adhesive, and the like. The conductors 712 can be attached to any suitable part of the electrodes 702, 704. For example, the conductors 712 can be attached to the interior surface or tabs of a segmented electrode 702 or the conductors 712 can be attached to an interior surface of the ring electrodes 704. The ring electrode 704 may include a notch 714 to facilitate attachment of the conductor 712. As described above, the conductors 712 are typically attached to terminals (not shown) disposed at a proximal end of the lead. A portion of the conductors proximal to the electrodes may be disposed in a sleeve 716 that can be formed of a polymer material. In at least some embodiments, the sleeve may form part of the lead body. In at least some embodiments, the sleeve 716 defines a central lumen (not shown) and one or more outer lumens (not shown) that carry the conductors 712. Optionally, the central lumen may accommodate a stylet.

Figure 7C:
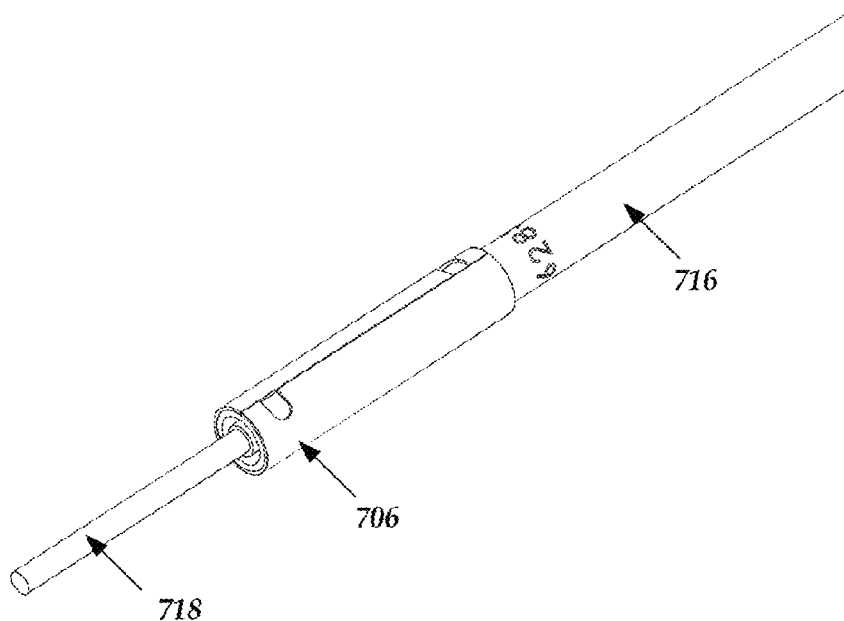
FIG. 7C is a schematic perspective view of the carrier and electrodes of FIG. 7B wrapped into a cylinder, according to the invention.

In step 606 (FIG. 6), the carrier 706 is formed into a cylinder, as illustrated, for example, in FIG. 7C. In at least some embodiments, the carrier 706, with the electrodes 702, 704 disposed thereon, is wrapped around a mandrel 718 to facilitate formation of the cylinder. The mandrel 718 may also be partially inserted into the sleeve 716 (e.g., into the central lumen of the sleeve) as illustrated in FIG. 7C. Although the embodiment illustrated in FIG. 7C shows a cylinder with a circular cross-section, it will be understood that other types of hollow rods can be formed including, but not limited to, hollow rods with square, rectangular, oval, triangular, hexagonal, or octagonal cross-sections.

The carrier can be held in the cylindrical form by any suitable method. In some embodiments, a forming tool that rolls the carrier into a cylinder facilitates maintenance of the cylindrical shape. In other embodiments, straps or fasteners may be attached to the carrier, or wrapped around the carrier, to hold it in the cylindrical form. Alternatively or additionally, two or more portions of the carrier (e.g., tabs 910 (FIG. 9A) and the corresponding opposing portion of the carrier) may overlap and the overlapping regions of the carrier can be attached to each other by welding, soldering, application of adhesive, or the like. In yet other embodiments, the carrier maintains its shape once formed into the shape.

Figure 7D:
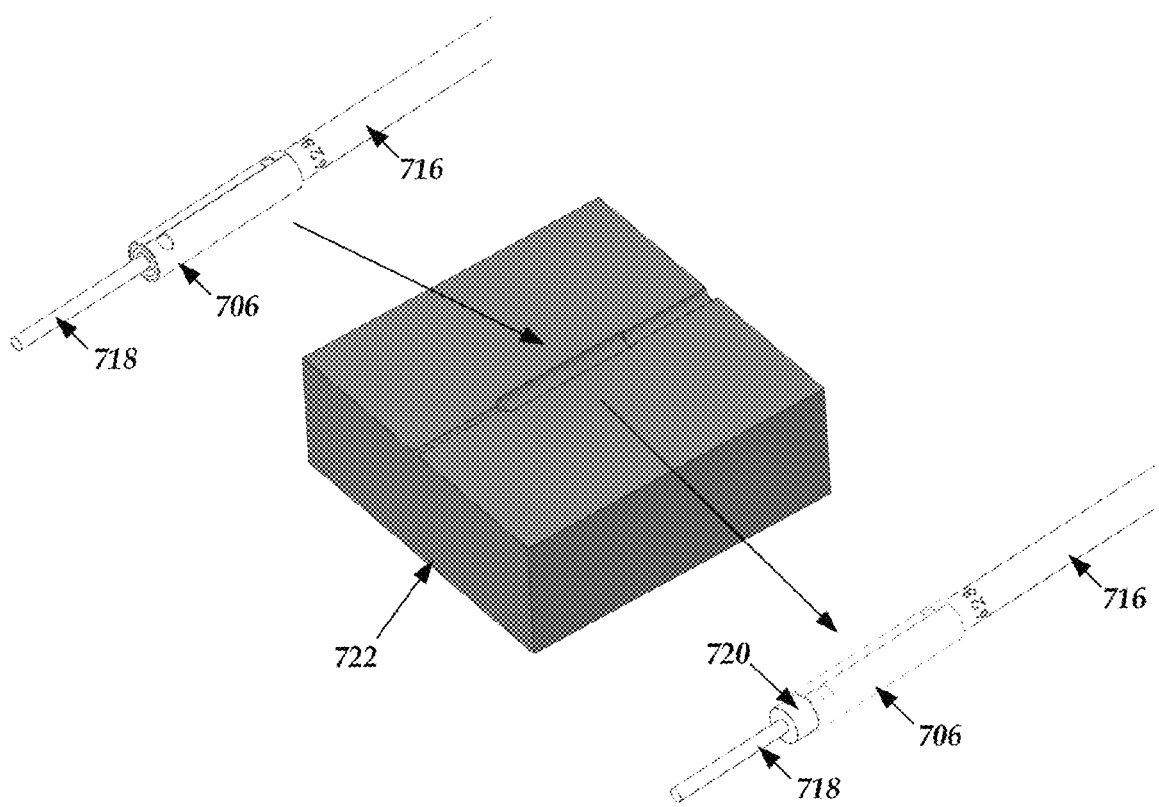
FIG. 7D is a schematic perspective view of steps in the molding of a lead body around the carrier and electrodes of FIG. 7C, according to the invention.

Once the carrier is formed into a cylinder, a lead body 720 is formed around the carrier 706 and electrodes 702, 704 (step 608). One example of the formation of the lead body 720 (FIG. 7E) is illustrated in FIG. 7D. In this example, the carrier 706 and the associated electrodes 702, 704 are disposed in a mold (only the bottom portion 722 of which is shown in FIG. 7D for ease of illustration). The mandrel 718 may remain in the assembly to maintain a central lumen within the lead. (A central lumen may be useful for receiving a stylet to aid in implantation or positioning of the lead.) When the carrier 706 and associated electrode 702, 704 are inserted in the mold and the mold is closed, plastic material is introduced into the mold to form the lead body 720. Any suitable molding technique can be used including, but not limited to, injection molding (e.g., rotary injection molding) and compression molding. The plastic material of the lead body 720 may cover all or a portion of the carrier 706 or, alternatively, may cover none of the carrier. The lead body 720 may cover all or a portion of the sleeve 716 that covers the conductors 712. (Alternatively, the conductors may not be disposed in a sleeve and the lead body is molded around the conductors as well as the carrier 706 and electrodes 702, 704.) Preferably, the material of the lead body is introduced beneath the carrier and is disposed around the electrodes 702, 704 so that at least the interior surfaces of the electrodes 702, 704 is in contact with the material of the lead body and the tabs, if any, extend into the material of the lead body.

Suitable materials for the lead body include biocompatible polymer materials, such as silicone, polyurethane, polyethylene, polyurea, polyurethane-urea, polyetheretherketone, and the like. The material introduced into the mold may be a polymer itself (for example, a polymer that has been heated to a fluid or semi-fluid state) or the material may be a pre-polymer material (e.g., monomers or oligomers) that is polymerized during the molding process. After forming the lead body, the assembly can be removed from the mold, as illustrated in FIG. 7D. Although the process has been described using a single molding step, it will be recognized that multiple molding steps, using the same or different materials, can be utilized in forming the lead body.

Figure 7E:
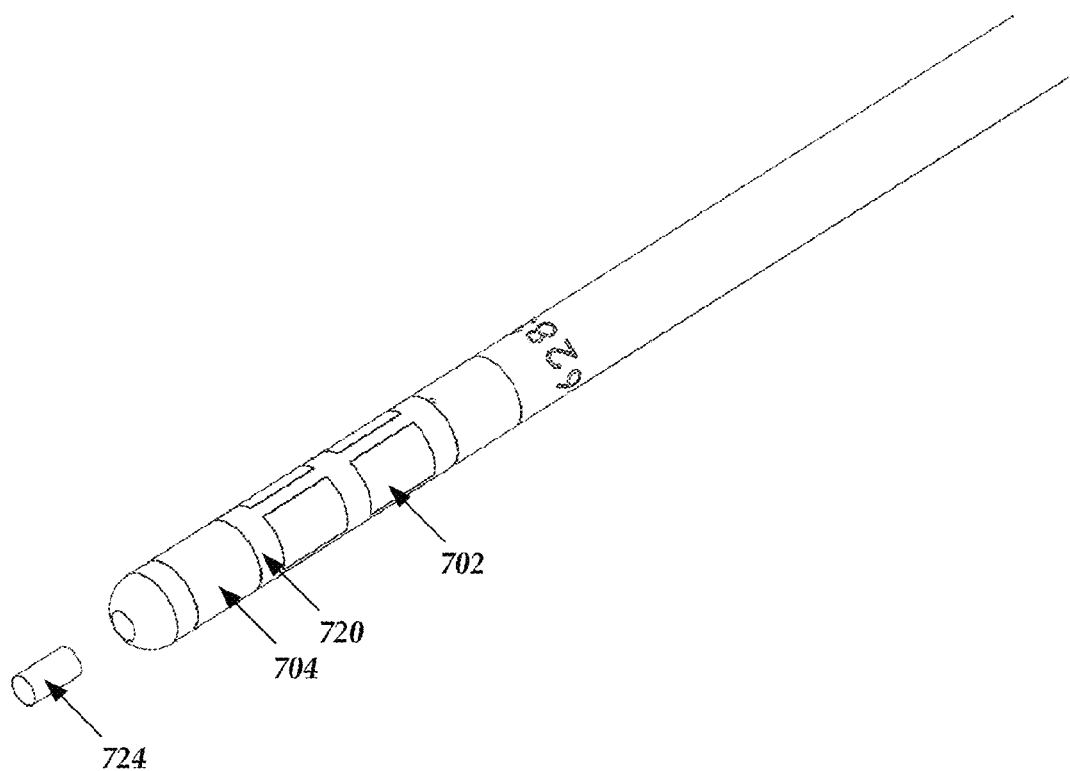
FIG. 7E is a schematic perspective view of a distal portion of a lead formed by the procedure illustrated in FIGS. 7A-7D, according to the invention.

Turning to step 610 (FIG. 6), the carrier 706 is removed leaving the electrodes 702, 704 disposed in the lead body, as illustrated, for example, in FIG. 7E. The carrier 706 can be removed by any suitable method such as, for example, grinding (e.g., centerless grinding), etching, cutting, degrading an adhesive to release the carrier, laser ablation, and the like. Suitable methods for removal of the carrier 706 may depend on the materials of the carrier and other components of the lead (for example, the electrodes 702, 704 and the lead body 720). In some embodiments, removal of the carrier 706 may also include removal of a small portion from the exposed surface of the electrodes 702, 704 to facilitate complete or nearly complete removal of the carrier. Alternatively, a portion of the carrier may be left on one or more of the electrodes.

In at least some embodiments, the mandrel 718 is removed prior to or after removal of the carrier. The removal of the mandrel leaves a central lumen. Optionally, a plug 724 of polymer (or other) material may be inserted into the distal end of the central lumen to close the lumen and prevent ingress of body fluids into the lumen when the lead is implanted. Optionally, the plug may be reflowed by heating, or adhesive can be used, to secure the plug in the lead body.

Figure 9A:
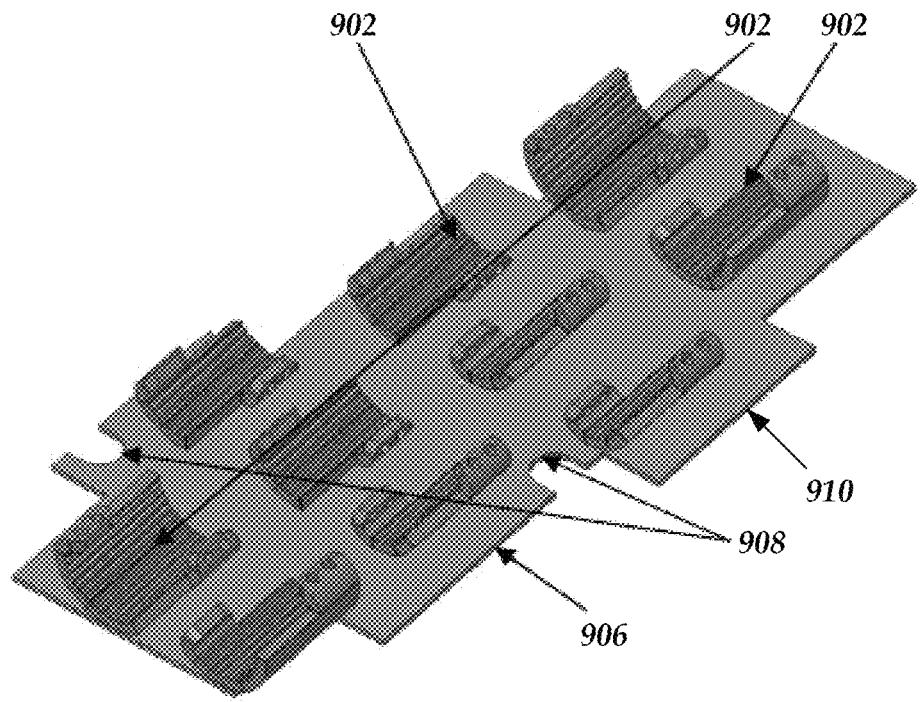
FIG. 9A is a schematic perspective view of another embodiment of electrodes disposed on a carrier, according to the invention.
Figure 9B:
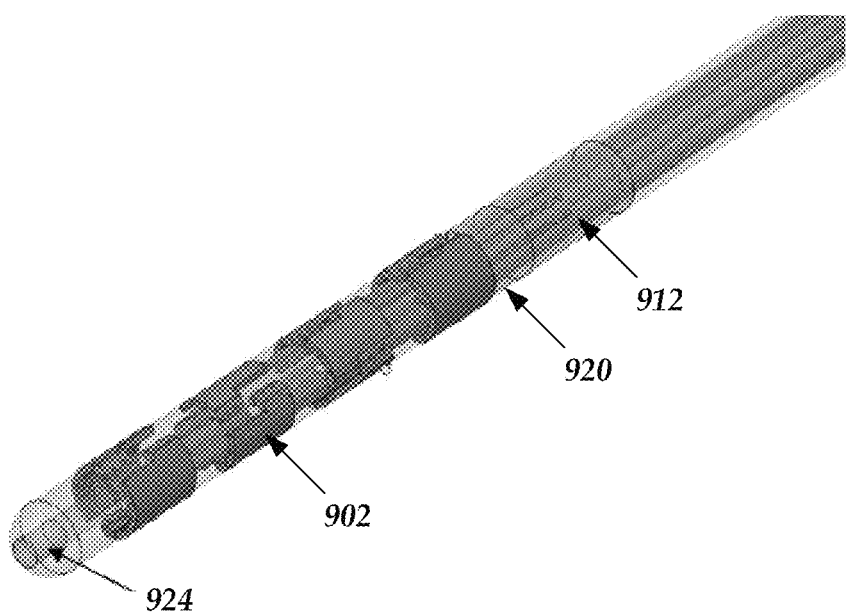
FIG. 9B is a schematic perspective view of conductors attached to the electrodes of FIG. 9A, according to the invention.

As indicated above any arrangement of electrode including segmented electrodes can be used. FIGS. 9A and 9B illustrate another arrangement of electrodes. FIG. 9A illustrates a carrier 906 with only segmented electrodes 902a, 902b disposed on the carrier. In the particular illustrated embodiment, segmented electrodes 902a form two groups of three circumferentially distributed electrodes and segmented electrodes 902b form two groups of two circumferentially distributed electrodes. The distal end of the final lead is illustrated in FIG. 9B. Although each of the electrodes could be attached to a different conductor and associated terminal, in at least some embodiments, two or more of the electrodes are attached electrically coupled to the same conductor. For example, the group of two electrodes 902b at the distal end can be electrically coupled to the same conductor (e.g., both directly attached to the same conductor or one attached to the conductor and a separate wire bridging the two electrodes). In addition, the group of two electrodes 902b at the proximal end can be electrically coupled to another one of the conductors. Examples of alternative electrode arrangements are discussed in U.S. patent application Ser. No. 12/761,622, incorporated herein by reference.

The above specification, examples, and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A method of making a stimulation lead, the method comprising:
    attaching a plurality of segmented electrodes to a carrier, each of the segmented electrodes has a curved rectangular form extending over an arc in the range of 10 to 345 degrees;
    attaching a plurality of conductors to the plurality of segmented electrodes;
    forming the carrier into a cylinder with the plurality of segmented electrodes disposed within the cylinder, wherein the carrier has at least one slot or tab formed on an edge or perimeter of the carrier to aid in alignment when the carrier is formed into the cylinder;
    molding a lead body around the plurality of segmented electrodes disposed on the carrier, wherein the plurality of segmented electrodes form at least two sets of segmented electrodes, wherein each of the at least two sets contains at least two of the segmented electrodes disposed around a circumference of the lead body at a same longitudinal position on the lead body; and
    removing at least a portion of the carrier to separate the segmented electrodes.

2. The method of claim 1, wherein removing at least a portion of the carrier comprises grinding the carrier to remove the portion of the carrier.

3. The method of claim 2, wherein grinding the carrier to remove the portion of the carrier comprises grinding all of the carrier away.

4. The method of claim 1, wherein the carrier is a metal or alloy carrier.

5. The method of claim 1, wherein molding the lead body comprises disposing the carrier and plurality of segmented electrodes in a mold and introducing a material into the mold to form the lead body.

6. The method of claim 1, further comprising attaching at least one ring electrode to the carrier.

7. The method of claim 6, where each of the at least one ring electrode has a notch in an edge of the ring electrode to facilitate attached of a conductor to the ring electrode.

8. The method of claim 1, wherein each of the segmented electrodes comprises a tab and wherein molding the lead body comprises molding the lead body around the segmented electrodes so that the tabs on the segmented electrodes extend into the lead body.

9. The method of claim 8, wherein the tab defines at least one hole through the tab.

10. The method of claim 1, wherein each of the segmented electrodes has a curved form extending over an arc in the range of 50 to 180 degrees.

11. The method of claim 1, wherein forming the carrier into a cylinder comprises forming the carrier into a cylinder around a mandrel.

12. The method of claim 1, wherein attaching the plurality of conductors to the plurality of segmented electrodes comprises attaching at least one of the plurality of conductors to each of the segmented electrodes.

13. The method of claim 1, wherein each of the segmented electrodes comprises a corrugated interior surface.

14. The method of claim 1, wherein each of the sets comprises at least three of the segmented electrodes.

15. The method of claim 14, further comprising attaching two ring electrodes to the carrier.

16. The method of claim 15, wherein one of the two ring electrodes is disposed distal to all of the segmented electrodes and another of the two ring electrodes is disposed proximal to all of the segmented electrodes.

17. The method of claim 1, wherein each of the segmented electrodes comprises two tabs disposed on opposite ends of the segmented electrode and wherein molding the lead body comprises molding the lead body around the segmented electrodes so that the tabs on the segmented electrodes extend into the lead body.

18. The method of claim 1, wherein carrier comprises two slots or tabs formed in the carrier opposite each other to aid in alignment when the carrier is formed into a cylinder.

* * * * *